United States Patent [19]

Shimizu

[11] Patent Number: 4,878,312
[45] Date of Patent: Nov. 7, 1989

[54] METHOD FOR CULTURING AND CULTIVATING FUNGI

[75] Inventor: Michitaka Shimizu, Showa, Japan
[73] Assignee: Compex Co., Ltd., Tokyo, Japan
[21] Appl. No.: 225,647
[22] Filed: Jul. 28, 1988

Related U.S. Application Data

[63] Continuation of Ser. No. 716,375, Mar. 26, 1985, abandoned.

[30] Foreign Application Priority Data

Mar. 30, 1984 [JP] Japan .................................. 59-61037

[51] Int. Cl.$^4$ .......................... A01G 1/04; C12N 1/14; C12Q 1/24
[52] U.S. Cl. ....................................... 47/1.1; 435/254; 435/30
[58] Field of Search .................. 47/1.1; 435/254, 242, 435/243, 30, 31, 911

[56] References Cited

U.S. PATENT DOCUMENTS

| | | | |
|---|---|---|---|
| 4,027,427 | 6/1977 | Staller et al. | 47/1.1 |
| 4,127,965 | 12/1978 | Mee | 47/1.1 |
| 4,280,000 | 7/1981 | Kozak, Jr. et al. | 435/254 X |
| 4,311,477 | 1/1982 | Kitamura et al. | 47/1.1 X |

FOREIGN PATENT DOCUMENTS

| | | | |
|---|---|---|---|
| 50-10222 | 4/1975 | Japan | 47/1.1 |
| 3050689 | 11/1983 | Japan | 47/1.1 |
| 207519 | 10/1985 | Japan | |

OTHER PUBLICATIONS

San Antonio, Hort Science, vol. 16(2), Apr. 1981, pp. 151–156.

*Primary Examiner*—Robert J. Warden
*Assistant Examiner*—Randall E. Deck
*Attorney, Agent, or Firm*—Oblon, Fisher, Spivak, McClelland & Maier

[57] ABSTRACT

In a method for culturing and cultivating fungi according to the present invention, the woods with the small diameter are used as the host woods. Into these woods with the small diameter, the fungi are inoculated through a cellulose sheet. The inoculated fungi are cultured and cultivated in a plastic bag having a porous site.

According to the culture and cultivation method of the present invention, the mushroom of high quality can be harvested in a very short period.

9 Claims, 2 Drawing Sheets

METHOD FOR CULTURING AND CULTIVATING FUNGI

This application is a continuation of application Ser. No. 06/716,375, filed on Mar. 26, 1985, now abandoned.

BACKGROUND OF THE INVENTION

The present invention relates to an improved method for culturing and cultivating fungi.

Hitherto, the mushroom such as *Lentinus edodes* has been cultivated by inoculating mushroom fungi into a host wood with a diameter of 10 cm or above and a length of about 100 cm, allowing to stand the inoculated host wood under suitable conditions until the hyphae grow and spread in the host wood and growing or cultivating the mushroom. Such a host wood is available with difficulty due to the fact that the supply of the wood with the diameter of more than 10 cm cannot be overtaken with its excessive demand. And, the wood with the diameter of less than 10 cm, especially less than 7 cm is unsuitable as the host wood since the regulation of the moisture, which is the very important factor in the culture of the fungi, is very difficult and always failed, thereby the fungi inoculated in the host wood cannot be cultured satisfactorily and successfully because of the lack of moisture.

The use of sawdust instead of the host wood in the above method has been proposed and practically effected on the industrial scale. As mentioned above, the culture conditions, for example, the temperature, humidity, light and so on are required to be carefully regulated for culturing the fungi and this requirement is, of course, applied to in the culture method using the sawdust as the culture medium.

For easily and successfully regulating the culture conditions whose regulation is very difficult and troublesome the use of a plastic bag having a porous site has been proposed by the present inventor (Japanese Patent Publication No. 42287/82). That is, this method comprises (a) introducing a culture medium which mainly consists of the sawdust into the plastic bag having the porous site;
(b) sterilizing the bag;
(c) inoculating the fungi into the medium; and
(d) sealing the bag and culturing the fungi.

The characteristics of the above-mentioned culture method are to use the plastic film having the porous site which acts to prevent the culture medium from contaminating with the unacceptable bacteria while supplying air in an amount necessary and sufficient for the growing of the fungi to the culture medium. Owing to the characteristics, the above-mentioned method has the following advantages and is highly evaluated:

(1) the conditions are successfully regulated during the culture of the fungi. In particular, the evaporation of the moisture is only a little;
(2) the suitable volume of air is supplied to the culture medium;
(3) the specific technics are unnecessary for the culture of the fungi; and
(4) the mushroom can be cultivated in very short period (some months), although at least some years are necessary until the harvest in the prior culture and cultivation method.

There are two important demerits derived from the use of the sawdust as the culture medium in the above-mentioned method, however, although it has many advantages. One is that the grade in quality of the harvested mushroom is lower as compared with that of the mushroom harvested by using the host wood as the culture medium. The other is that the sawdust amount is not enough to meet its demand and accordingly to use the sawdust as the culture medium, it is necessary to take a special time and cost for making the sawdust.

An object of the present invention is to dissolve the above-mentioned demerits without impairing the advantages in the culture and cultivation method using the plastic bag having the porous site.

Another object of the present invention is to provide the culture and cultivation method using as the culture medium the wood with the diameter of less than 10 cm which had been thrown away as the worthless until now.

Another object of the present invention is to provide the mushroom with high grade in quality.

These and other objects of the present invention will be apparent from the following descriptions.

SUMMARY OF THE INVENTION

The method for culturing and cultivating the fungi according to the present invention is characterized in that the host wood with a small diameter is used as the culture medium and that the fungi are inoculated into the host wood through a cellulose sheet.

Figure 1:
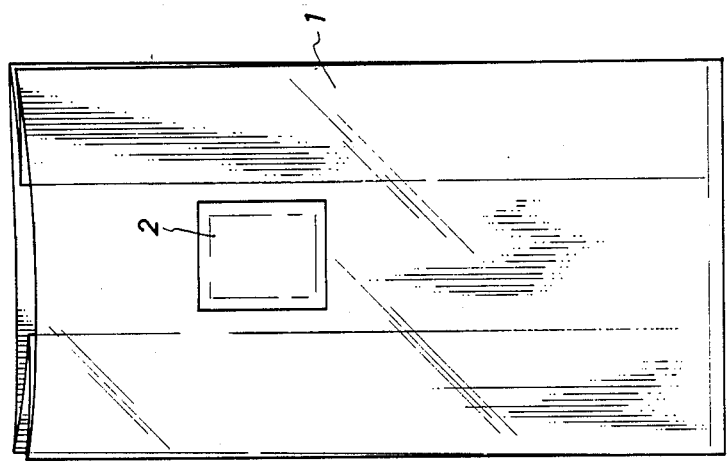
FIG. 1 is the view of the plastic bag used in the present invention.

DETAILED DESCRIPTION OF THE INVENTION:

As shown in FIG. 1, the plastic bag (1) used in the present invention has the porous site (2). The plastic bag is made of a plastic having the heat durability so as to be capable of resisting high temperature during the following sterilization step and the strength so as to be capable of resisting the impacts on introducing the host woods into the plastic bag. Generally, the film of polyolefin polyvinyl chloride, polyester, nylon and the like in the thickness of 30 to 150 microns is used. Preferably, the tubular film of polyolefin of the thickness of about 50 to 100 microns is used owing to its low water vapor permeability and its good oxygen permeability. The plastic film in which any additive is incorporated may be used. Especially, the use of the translucent plastic film controls the light quantity, thereby the growing rate of the fungi being increased. The plastic film is made into the plastic bag by any conventional bag making machine such as a gusset-type bag making machine. The size and the form of the plastic bag are no particularly limited and are freely determined.

The porous site (2) acts to prevent the passing-through of the unacceptable bacteria while supplying air suitably and has the heat durability so as to be capable of resisting high temperature during the following sterilization step. The porous site is not particularly limited with respect to the material if the action and the nature mentioned above are not impaired. Usually, a porous plastic film a non-woven fabric, a resin-treated paper, a compressed urethane foam sheet, a fiber cloth and the like are used. The microporous plastic film having 0.1 to 1 micron in mean pore size is preferably used. The size of the porous site is determined by the volume of the host wood and is generally 0.5 to 100 cm$^2$ per 1 liter of the host wood volume. In a case of the above-mentioned size being larger, the moisture is evaporated from the host wood excessively and as the result the fungi do not grow satisfactorily. On the other hand, in a case of the above-mentioned size being smaller, the air cannot be supplied sufficiently and as the result the growing of the fungi is not satisfactory, too. The preferable size of the porous site is 0.5 to 10 cm$^2$/1 liter of the host wood volume.

The manner for providing the porous site on the plastic bag is not particularly limited. For example a part of the plastic bag is cut off and then the porous plastic film in a size larger than the cut-off part of the plastic bag is adhered with any adhesive or through heat.

The culture medium in the present invention is wood (3) with the diameter of about 1 to 10 cm and the length of about 10 to 100 cm, that is, a twig which is thought for those skilled in the art not to be available as the host wood and is left in the woodlands as it is. Various woods employed in the conventional culture and cultivation method as the host woods can be also employed in the present invention Usually, *Quercus serrata, Castanopsis cuspidata, Fagus crenata, Quercus dentata* and the like are employed as the host wood.

Figure 2:
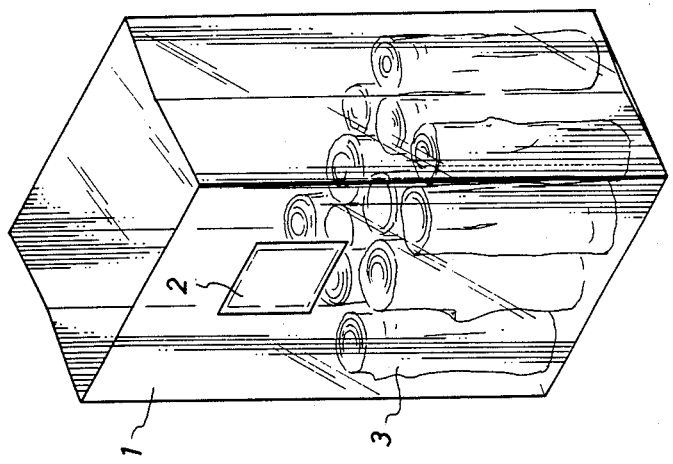
FIG. 2 shows the state of introducing the host woods into the plastic bag of FIG. 1.

In the present invention, at least one of the twigs mentioned above is introduced into the plastic bag. Conveniently, a plurality of twigs are introduced thereinto after bundling with, for example, a string or a band, as shown in FIG. 2.

Figure 3:
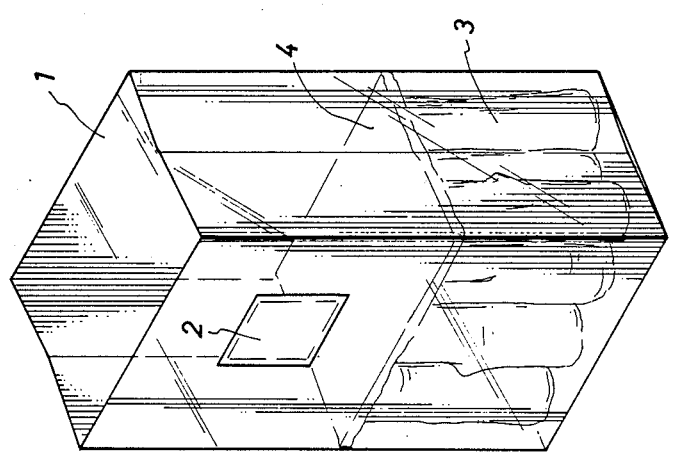
FIG. 3 shows the state of providing the cellulose sheet on the host woods.

Following the introduction of the host woods into the plastic bag, the cellulose sheet (4) is put on the host woods in the bag. However, it is possible to put the cellulose sheet at the bottom of the plastic bag prior to the introduction of the host woods into the bag. And, it is also possible to put the cellulose sheet on and under the host woods. This sheet is preferably put on the host woods, as shown in FIG. 3. This cellulose sheet may be a cardboard, a pasteboard, a pulp-molding sheet or a non-woven fiber cloth having the thickness of 0.5 to 5 mm, and the nutrients such as glucose cornstarch, malt extract and the like may be added therein if necessary. Further, a bactericide, a mineral, an absorbable high molecular material and the like may be present. If the sheet is put at the bottom of the bag, the risk of breaking the bag on the introduction of the host woods will be reduced. For culturing the fungi more speedily, it is preferable to use the cellulose sheet in which water is absorbed adequately in advance.

Following the introduction of the cellulose sheet and the temporary sealing of the bag, the bag is subjected to the sterilization with steam. On the sterilization, the cellulose sheet closely fits on the host woods. In addition, the unacceptable bacterium are killed and the vital cells in the woods are also destroyed and therefore, the condition of the host wood is very suitable and preferable for the culture of the fungi.

Then, the fungi are inoculated in the host woods through the cellulose sheet after cooling the bag to the temperature suitable for the inoculation of the fungi. The inoculation of the fungi through the cellulose sheet constitutes one of the characteristic features in the present invention.

Figure 4:
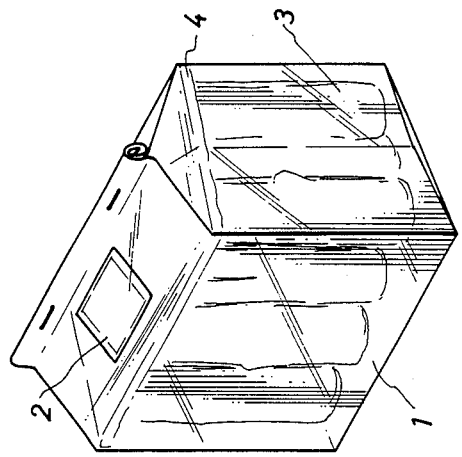
FIG. 4 shows the state of culturing the fungi after their inoculation into the host woods.

The steps following the inoculation of the fungi are carried out in the same manner as the conventional culture and cultivation method using the sawdust and the plastic bag. Firstly, the bag is sealed simply, for example by a stapler and the fungi are cultured under a given condition until the hyphae grow and spread through the host woods, as shown in FIG. 4. In this stage, the mouth of the bag may be cut and the mushroom may be cultivated in the same manner as the cultivation method using the host woods with large diameter without the use of the plastic film.

The culture and cultivation method according to the mushroom fungi such as *Lentinus edodes., Pholiota nameko., Pleurotus ostreatus, Panellus ostreatus, Pleurotus cornucopiae, Lyophyllum ulmarium., Flammulina velutipes, Naematoloma sublateritium, Grifola frondosa., Grifola umbellata, Coriolus versicolor., Coriolus hirsutus., Canoderma lucidum., Hericium erinaceum, Auricularia auricula-judae., Tremella fuciformis.,* and *Tremella foliacea.*

Even if the wood with the small diameter which easily evaporates the moisture is used as the host wood in the present invention, the excessive evaporation of the moisture can be prevented by the use of the plastic bag having the porous site, thereby the fungi inoculated can grow successfully and satisfactorily. In this way, the wood with the small diameter is available in the present invention. This fact is very significant since the woods with the small diameter used only as the fuel until now is found to be as the worth material. Further, in compared with the use of the sawdust, the use of the woods with the small diameter in the present invention gives many advantages. For example, the mushroom having the quality equal to that of the mushroom harvested by the conventional culture and cultivation method using the host woods with the large diameter can be harvested. The woods left alone in the woodlands can be used as the culture medium without any special operation and step, while in the sawdust, the special step of making the sawdust is necessary as mentioned above. In addition, the time necessary for sterilizing the woods is very short (as compared with the sawdust the sterilization time is reduced by about half). As clear from the above-mentioned, the use of the woods with the small diameter can provide not only the novel and epochal method for culturing and cultivating fungi, but also the economical fungi culture and cultivation method.

Moreover, the inoculation of the fungi through the cellulose sheet can give many advantages, too. One is that the special technique for inoculating the fungi is unnecessary, while in the conventional culture method using the host woods, the so-called seed bullets are necessarily implanted in the host woods to inoculate the fungi and this implantation is the important and difficult work and the special technique is also required thereto. Therefore, it is possible for the non-professional to culture and cultivate the fungi employing the culture and cultivation method according to the present invention. And, since the position of the woods in which the fungus is inoculated is not particularly limited owing to the use of the cellulose sheet, the fungi can be inoculated everywhere in the host woods and the hyphae can grow and spread through the woods more speedily and quickly. As the result, the culture period can be shortened and it is possible to harvest the mushroom several times in a year and improve the harvest of the mushroom.

Now the present invention is described with reference to the following example.

EXAMPLE

A tubular polypropylene film of 80 microns thickness and 65 cm lay-flat width was made into a bag of 35 cm width and 150 cm length by folding each 15 cm of both sides of the film and by heat-sealing the bottom using a gusset-type bag making machine. Further, a microporous polypropylene film (trade name: Juraguard #4510, a product of Celanese Chemical Co., in U.S.A.) site of about 28 cm$^2$ in effective area, whose micropore is 0.2 micron in size and whose porosity is 45%, was provided on a somewhat higher position of the bag. The piled portion of the polypropylene film bag with the microporous polypropylene film was perforated in the form of a circle of 4 cm diameter, and the residual piled portion was allowed to adhere by means of an impulse sealer.

The plastic bag so produced was allowed to stand in the form of column of 35 cm width and 30 cm depth. A pulpmolding sheet of 35×30 cm was placed on the bottom of the plastic bag. On the other hand, 30 host woods with the 5 cm diameter and 60 cm length were bundled in the form of 5 rows×6 rows. The woods so bundled were introduced into the plastic bag and a cellulose sheet allowed to absorb water sufficiently was laced on the woods. Then, the bag was sealed temporarily and sterilized at 95° C. for 3 hours with steam. After cooled, mushroom fungi were inoculated on the cellulose sheet and cultured at about 20° C. for 2 months. As the result, white hyphae were found throughout the total surface of the host woods After the conclusion of the culture step, the host woods were taken out of the bag and placed at 10° to 20° C. for 1.5 month in the shade of trees to cultivate mushroom.

As the result, about 3 kg of mushroom per a bag was harvested. The mushroom so obtained has the quality equal to that cultivated with the host woods of the diameter of more than 10 cm.

What is claimed is:

1. A method for culturing and cultivating fungi, comprising the steps of:
   (a) introducing at least one host wood piece having a diameter of 1 to 10 cm into a plastic bag having a porous site therein;
   (b) placing at least one cellulose sheet to promote inoculation of the fungi and to promote the culture and cultivation of the fungi, which contains nutrients and a bactericide, on said at least one host wood piece in the bag;
   (c) sterilizing the bag;
   (d) inoculating the cellulose sheet with the fungi; and
   (e) sealing the bag and culturing the fungi.
2. The method according to claim 1, wherein the fungi are fungi of an edible mushroom or a medicinal mushroom.
3. The method according to claim 2, wherein the cellulose sheet is a cardboard, a pasteboard, a pulpmolding sheet or a non-woven fiber cloth.
4. The method according to claim 1, which further comprises placing a second cellulose sheet underneath the host wood in order to prevent the risk of breaking the bag upon the introduction of the host wood into the bag.
5. The method according to claim 1, wherein said cellulose sheet has a thickness of 0.5 to 5 mm.
6. The method according to claim 1, wherein said fungi is a species selected from the group consisting of *Lentinus edodes, Pholiota nameko, Pleurotus ostreatus, Panellus ostreatus, Pleurotus cornucopiae, Lyophyllum ulmarium, Flammulina velutipes, Maematoloma sublateritium, Grifola frondosa, Grifola umbellata, Coriolus versicolor, Coriolus hirsutus, Canoderma lucidum, Hericium erinaceum, Auricularia auriculajudae, Tremella fuciformis* and *Tremella foliacea.*
7. The method according to claim 1, wherein the size of said porous site is 0.5 to 100 cm$^2$ per liter of host wood volume.
8. The method according to claim 1, wherein the plastic material of said plastic bag is a polyolefin, polyvinyl chloride, a polyester, or nylon.
9. The method according to claim 1, wherein the thickness of the plastic bag ranges from 30 to 150 microns.

* * * * *